United States Patent [19]
Hughes et al.

[11] Patent Number: 4,849,593
[45] Date of Patent: Jul. 18, 1989

[54] MICROWAVE-ACTIVATED HEATING ELEMENT

[76] Inventors: Thomas E. Hughes, P.O. Box 634, Fairhope, Ala. 36533; Calvin L. Seals, 908 Dauphine Cir., Daphne, Ala. 36526

[21] Appl. No.: 29,663

[22] Filed: Mar. 24, 1987

Related U.S. Application Data

[63] Continuation-in-part of Ser. No. 918,729, Oct. 14, 1986, Pat. No. 4,743,726.

[51] Int. Cl.⁴ .............................................. H05B 6/64
[52] U.S. Cl. ...................... 219/10.55 R; 219/10.55 F; 132/229
[58] Field of Search ................. 219/10.55 E, 10.55 R, 219/10.55 M, 10.55 F; 132/33 R

[56] References Cited

U.S. PATENT DOCUMENTS 4,538,630 0/1985 Henderson .................... 219/10.55 R
4,743,726 5/1988 Hughes et al. ................ 219/10.55 F

FOREIGN PATENT DOCUMENTS

DE3148538 6/1983 Fed. Rep. of Germany.

Primary Examiner—Robert S. Macon
Attorney, Agent, or Firm—Nixon & Vanderhye

[57] ABSTRACT

A heating element for retaining heat applied by reaction with high-frequency microwave radiation is provided in various forms. In one form, the heating element includes a multi-layered cartridge having a center core for dissipating heat, a layer of material reactive to microwave radiation for retaining heat and an outer layer of paper for substantially sealing the cartridge, yet permitting heat to radiate in use from the cartridge. In another form, the heating element has multiple layers formed of a rubber and cellular material for retaining water, the multiple layers being disposed about a central core of wax material. In a still further form, the heating element may comprise clay disposed within a covering, the clay containing minerals or aromatics, depending upon its use. In all such heating elements, the materials comprising the elements are reactive to high-frequency microwave radiation to retain heat and radiate such retained heat upon application for their intended purposes.

29 Claims, 4 Drawing Sheets

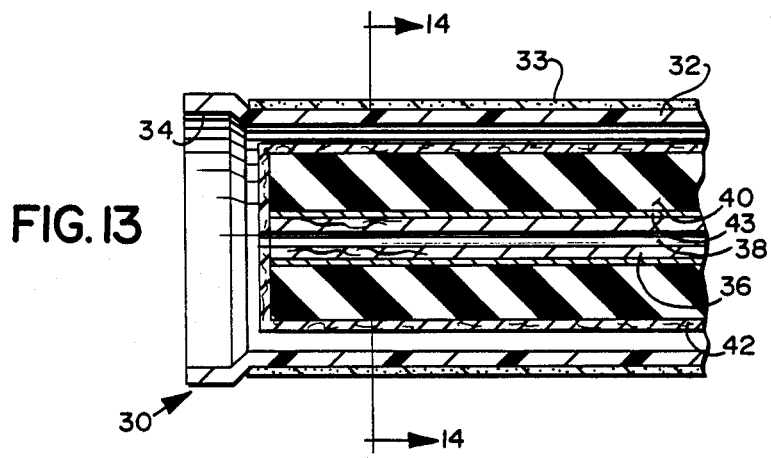
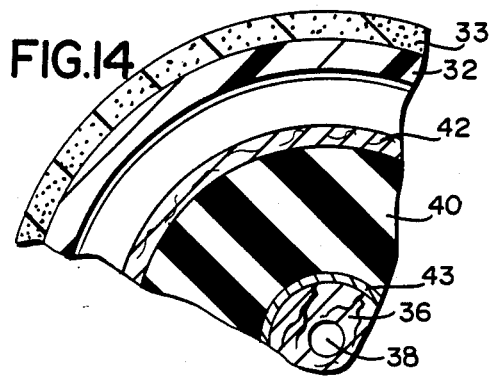
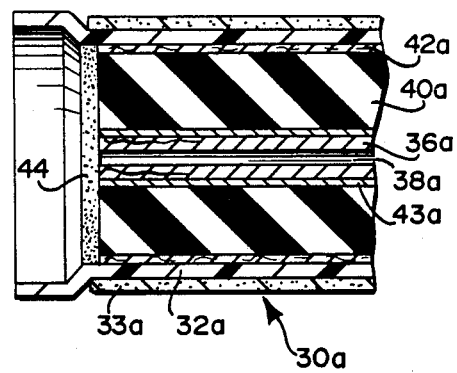
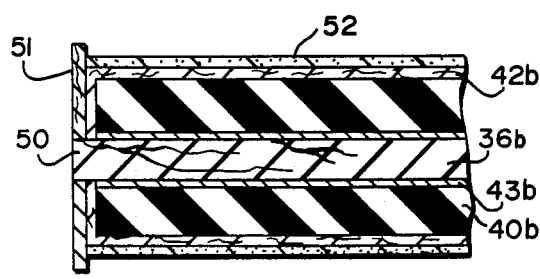
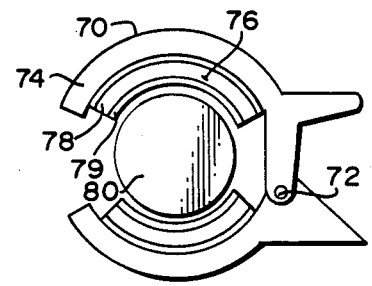

MICROWAVE-ACTIVATED HEATING ELEMENT

This application is a continuation-in-part of application Ser. No. 918,729, filed Oct. 14, 1986, now U.S. Pat. No. 4,743,726 issued May 10, 1988.

The present invention relates to hair, skin, and beauty care products, as well as medical and therapeutic products and appliances which are required to be heated in order to apply radiant heat when performing their intended function. Particularly, the present invention relates to such products designed specifically to be heated by high-frequency microwave radiation.

Various products and appliances in the hair, skin, and beauty care, as well as medical and therapeutic fields, are required to be heated preliminary to their application, which usually involves applying radiant heat. To heat such products and appliances prior to use, electrical heating elements are generally used. These require the continuous availability of electrical current throughout the period of use. In the course of that use, the appliance can malfunction, overheat, short-out or, when unattended, result in a burnout of the appliance or a fire.

In those products which are heated and then removed from the source of electrical current prior to their application, there is a problem in that the product may not retain sufficient heat for a sufficient length of time to adequately perform its intended function. For example, in the home hair care field, rollers are conventionally disposed over electric heating elements for a period of time whereby the heating elements heat the rollers. The rollers are then removed from the heating elements and applied to the hair. Substantial heat is lost from the roller in the course of removing it from the electrical heating element and applying it to the hair. To prevent this, the roller may be heated to a temperature substantially higher than needed in its application and this, by itself, may cause additional problems. Moreover, most home hair care rollers presently available are formed of plastic material and these do not have particularly high, long-term heat retention characteristics. Additionally, electrical heating elements normally require an extended period of time in which to heat the rollers, which correspondingly and undesirably extends the time required for completing the hair treatment.

When using medical and therapeutic products, similar problems arise. For example, a conventional heating pad requires the application of continuous electrical current in order to maintain sufficient heat for therapeutic purposes. The individual using the heating pad must therefore have a continuous and readily available source of electrical current. It has not yet been practical to remove the heating pad from the electrical current source with the expectation that therapeutic results can be achieved because most heating pads are not designed to and simply do not retain sufficient heat at a sufficiently high temperature over the desired time period to achieve the intended therapeutic results.

According to the present invention, there is provided, in various forms, a microwave-activated heating element for use in connection with appliances used in related and diverse fields, such as the hair, skin, and beauty care and medical and therapeutic fields, where controlled application of heat is required. For example, in the hair care field, the microwave-activated heating element hereof may take various forms including a reusable cartridge. The cartridge hereof is formed of materials highly reactive to high-frequency microwaves such that the temperature of the cartridge may be readily and quickly elevated. The cartridge is thus heated by subjecting it to high-frequency microwave radiation, as may be available, for example, in a microwave oven. After heating, it may be applied to a hair care product. For example, the heated cartridge may be inserted into a conventional hair roller comprised of a sleeve and the combination applied to an individual's hair in the usual manner The cartridge, by radiating heat, heats the sleeve which, in turn, heats the hair.

Various advantages accrue to such use. It has been found that the cartridge may be removed from the microwave oven, inserted into the hair roller and the hair rolled without danger of burning the individual's hands. That is to say, the cartridge can be freely handled for a predetermined sufficient time period before the heat retained in the cartridge radiantly penetrates its surrounding appliance. Moreover, it has been found that, by virtue of the construction of the cartridge, hot spots do not occur in the cartridge, or if formed integrally with the appliance, do not occur in the appliance. In short, there is no danger from overheating.

Particularly, in accordance with one form of the present invention, the cartridge may comprise a cylindrical multi-layer heating element including a core of wax material, a layer of open cellular water retaining material, a layer of rubber and an outer layer of paper. In this form, the rubber and water are heated by the high-frequency microwave radiation and the water in the cellular material, as well as the wax forming the central core, assist in retaining the heat in the cartridge.

In another and preferred form of the present invention, particularly for high-temperature applications above the boiling point of water, the cartridge may be comprised of a central core formed of a wood dowel, an annular overlay of rubber material with an appropriate high-temperature lubricant disposed therebetween, and an outer covering, for example, formed of paper. The outer paper permits the microwave radiation to penetrate the cartridge, permits heat to escape from the cartridge and substantially prevents air from entering the cartridge, thereby preventing combustion or flashing of the material of the cartridge. The paper further enables the cartridge to dissipate heat which might otherwise, in the microwave oven, cause a burning or flashing of the cartridge material. The rubber layer is reactive to the high-frequency microwave radiation and its temperature is quickly elevated in response to such radiation. It also serves to retain the heat and gives shape and rigidity to the cartridge. Because the wood dowel is porous, it serves to dissipate heat through its exposed ends. In a preferred form hereof, the wood dowel is provided with a central axial passage to further enhance the dissipation of heat when subjected to microwave radiation. Lubrication is provided between the rubber layer and the wood dowel for the purpose of promoting even spreading of the heat, retarding flaming, and enabling a higher build-up and tolerance of heat.

In a preferred form of the present invention, the cartridge may be a separate microwave heatable element, for example, removably insertable within a hair roller for transferring its radiant heat to the roller and hence to the rolled hair. Alternatively, it may be an integral pat of a hair roller. In the latter instance, the roller cartridge combination may be disposed in the microwave oven, heated and applied directly to the hair.

In the hair care field, the heating element hereof may take other forms. For example, a hair clip may be provided having arcuate sections for engaging opposite sides of a hair roller, the individual's hair being disposed about the roller. In this form, the sections are formed of a high carbon content rubber, with paper disposed on either side. The entire hair clip may be subjected to microwave radiation and subsequently applied about the rolled hair whereby its retained heat radiates from the clip into the hair about the roller.

In another form, the cartridge may be disposed inside an elongated Teflon ® sleeve for use as part of a hair curling iron. In this form, the wood dowel may extend beyond the ends of the sleeve for structural cooperation with the handle of a conventional hair curling iron, as well as to dissipate the heat from the heating element when disposed in the microwave oven.

In the medical and therapeutic product fields, the heating element of the present invention may take the form of a clay encapsulated within a covering material, such as plastic. An additional covering, for example terrycloth, may then be applied about the encapsulated clay, with the resulting product serving, for example, as a heating pad. This is particularly advantageous because clay has shape-retaining properties and thus the heating pad, after removal from a microwave oven, may be shaped to the contour of the area to which it is being applied. In other forms, the clay may be encapsulated in a porous membrane, such that the clay may have added medicinal compounds, aromatics, perfume or the like, depending on the specific application. For example, a buff pad may be provided, with the aromatics mixed in the clay, and enclosed by a plastic material open along one or more sides. Alternatively, the plastic material may be closed but perforated. A buff pad outer covering with an astringent may encapsulates the clay, with the aromatic or other compound mixed with the clay providing the desired effect upon use.

In another form of the present invention, there is provided a multi-layer microwave heatable element for use in hair care including a first layer formed of a material having heat dissipative properties, a second layer overlying the first layer and formed of clay, which is reactive to high frequency microwave radiation to rapidly elevate its temperature, and an outer layer of material overlying the second layer for maintaining the first and second layers substantially air tight and through which heat may be dissipated.

Accordingly, it is a primary object of the present invention to provide a novel and improved heating element reactive to high-frequency microwave radiation for use in various products in the hair, skin, beauty care and medical and therapeutic fields.

These and further objects and advantages of the present invention will become more apparent upon reference to the following specification, appended drawings and claims.

BRIEF DESCRIPTION OF THE DRAWING FIGURES

Figure 18:
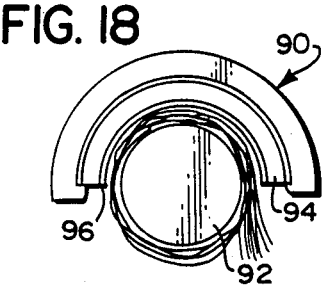
Figure 19:
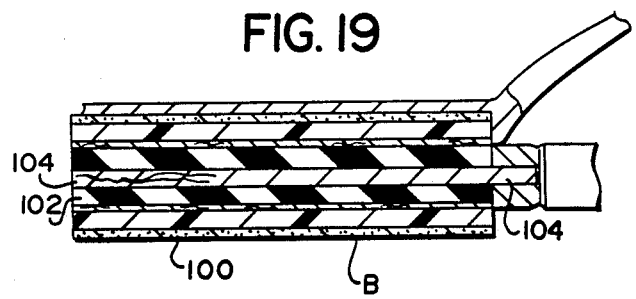
Figure 20:
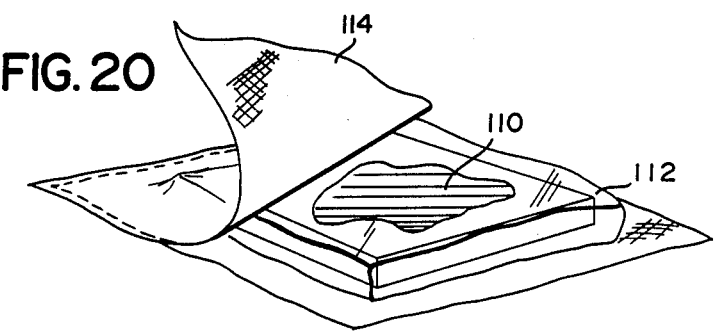
Figure 21:
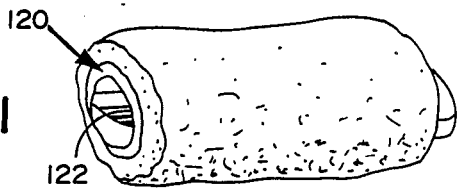
Figure 22A:
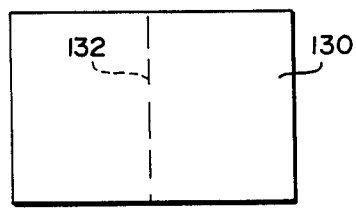
Figure 22B:
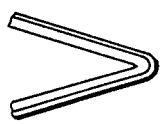

FIGS. 8 through 12 schematically illustrate various applications of the heating element of the present invention;

FIG. 13 is a longitudinal cross-sectional view of a further embodiment of a heating element constructed in accordance with the present invention and insertable within a hair roller;

FIG. 14 is a cross-sectional view thereof taken generally about on line 14—14 in FIG. 13;

FIG. 15 is a fragmentary cross-sectional view similar to FIG. 13, illustrating an end portion of a hair roller constructed in accordance with a still further form of the present invention;

FIG. 16 is a longitudinal cross-sectional view of a roller constructed in accordance with a still further form of the present invention;

FIG. 17 is a cross-sectional view of a hair clip using a heating element constructed in accordance with the present invention;

FIG. 18 is a cross-sectional view of a still further form of clip using a heating element of the present invention;

FIG. 19 is a longitudinal cross-sectional view of a portion of a curling iron using a heating element according to the present invention;

FIG. 20 is a cross-sectional view of a heating pad using a heating element according to the present invention;

FIG. 21 is a cross-sectional view of a buffing pad using a heating element according to the present invention; and FIGS. 22a and 22b illustrate a hair straightener employing a heating element according to the present invention.

DETAILED DESCRIPTION OF THE DRAWING FIGURES

Figure 1:
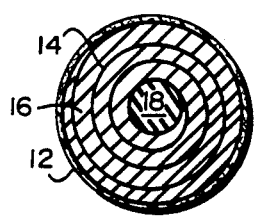
FIG. 1 is a cross-sectional view of a heating element constructed in accordance with the present invention and taken generally about on line 1—1 in FIG. 2.
Figure 2:
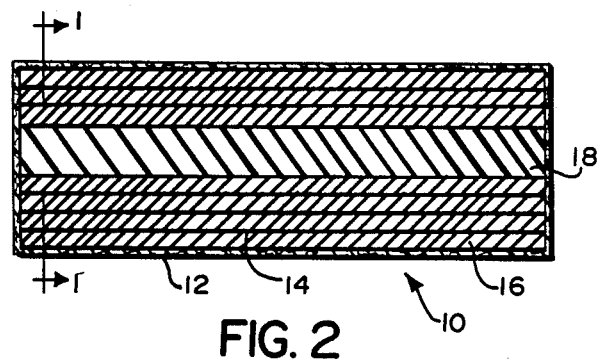
FIG. 2 is a longitudinal cross-sectional view of heating element constructed in accordance with the present invention.

Referring now to the drawings, particularly to FIGS. 1 and 2, there is illustrated a preferred form of a heating element, constructed in accordance with the present invention, and comprising a cartridge, generally designated 10, which is concentrically wound to form a multi-layered heating element. Particularly, heating element cartridge 10 is encased within an outer layer 12 of material readily penetrated by high-frequency microwave radiation for heating internal elements and which layer substantially seals the internal elements of the cartridge. Such layer may be comprised of a cellulosic material, such as kraft or fish paper. A layer 14 of heat and flame-resistant rubber having a high temperature lubricant applied on opposite sides thereof is spirally wound with layers 16 of cellular material saturated with water or mineral oil. Layers 14 and 16 are wound spirally about a center core 18 formed of a wax material having a high melting point.

More particularly, the outer paper covering 12 is preferably treated to be water and oil resistant, maintains the interior elements of the cartridge in substantially an airtight condition and permits high-frequency microwave radiation to penetrate it to cause rapid heat buildup within cartridge 10. By forming a substantially airtight enclosure, combustion of the internal materials is retarded or prevented. The rubber forming the layer 14 is preferably a Butadene Nitrile. This rubber material serves to retain heat generated by the microwave radiation, retains water in cellular layer 16 and gives shape and rigidity to the cartridge. The rubber is lubricated both on its inside and outside surfaces with a high temperature oil-base lubrication. The purpose of the lubrication is to promote the even spreading of heat, retard flaming and permit higher buildup and tolerance of heat, as well as to suppress combustion and smoking. The cellular material of layer 16 may comprise any open-cell material that can suspend water. The central wax core 18 is generally not reactive to microwave radiation but will absorb heat from the superimposed layered material. Thus, the wax material melts and gives up its stored heat in use.

Figure 3:
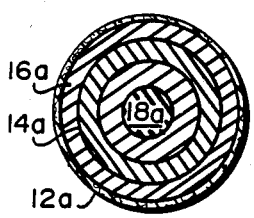
FIGS. 3 and 4 are views similar to FIGS. 1 and 2, respectively, illustrating a further form of the heating element hereof.
Figure 4:
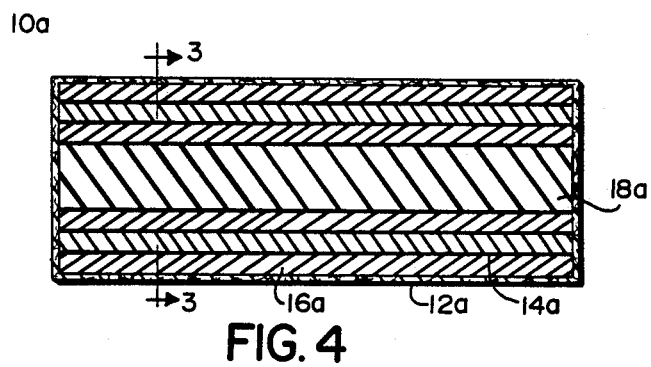

In FIGS. 3 and 4, similar elements are denoted by like reference numerals followed by the suffix "a". In this form, the heating element cartridge 10a is similar in construction to the cartridge 10 of FIGS. 1 and 2, except that cartridge 10a is comprised of concentric layers of rubber and cellular material 14a and 16a, respectively, encapsulating a central wax core 18a. All layers are covered by an outer layer 12a of paper.

In using these heating elements or cartridges 10 or 10a, they are exposed to a source of high-frequency microwave radiation, for example, they may be disposed in a microwave oven. As the microwaves pass through the outer paper covering 12 or 12a, the molecules of the successive internal layers react and cause a rapid buildup of heat to occur, first in the water molecules in the cellular layer 16 or 16a. A slower increase in temperature is effected in rubber layer 14 or 14a. The buildup of heat in the rubber layer continues after the microwave radiation has ceased. The wax central core 18 or 18a does not respond directly to the microwave energy but does absorb heat generated from the rubber and water, affording a heat retention feature in the center of the heating element. Thus, after the cartridge is removed from the microwave oven, the melted wax releases its stored heat slowly and gradually returns to its solid condition.

Figure 8:
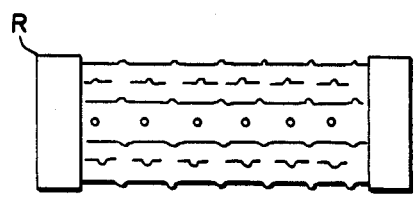

Characteristic of these heating elements or cartridges is their ability to be removed from the microwave oven without regard for the temperature of their outer covering. That is, the outer covering does not, at least initially, have an elevated temperature and thus the cartridge can be handled immediately after the microwave radiation is terminated. However, cartridge 10 or 10a will begin to radiate sufficient heat soon after removal from the microwave. Thus, in use, for example, in conjunction with a hair roller as illustrated in FIG. 8, the cartridge may be removed from the microwave oven and inserted into the cylindrical opening of the hair roller. Suitable releasable retention means, not shown, may be provided in the roller, if desired. Upon insertion of the cartridge into the roller, the roller is then applied to an individual's hair. At that time, heat from cartridge 10 or 10a radiates outwardly through its paper covering into the roller material, usually plastic, and then outwardly from the roller into the hair. The heat retention characteristics of the cartridge are such that heat is applied to the hair for a period of time approximately two and three times longer than conventional electrically-heated rollers and at the temperature required to properly effect curling of the hair.

Figure 5:
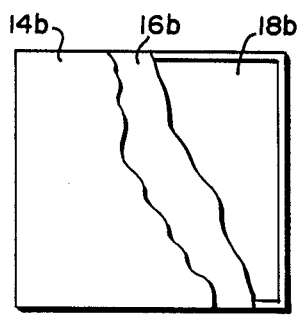
FIG. 5 is a plan view of a layered heating element, with parts broken out and in cross-section, forming a further embodiment of the present invention.
Figure 6:
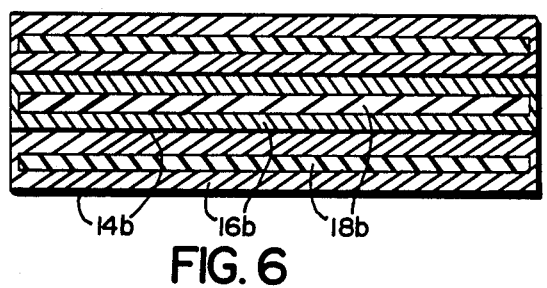
FIG. 6 is a cross-sectional view thereof.

Referring now to FIGS. 5 and 6, like reference numerals as applied in the embodiments of FIGS. 1 and 3 denote like parts followed by the suffix "b". In this form, the heating element is provided in flat sheets of layered material and which layers may be repeated throughout the depth of the heating element. The layers may be sealed about the edges and the entire layered heating element enclosed within a covering, for example, a terrycloth material, whereby the layered heating element may be used as a heating pad. More particularly, and as illustrated in FIG. 6, the layers repeat and comprise, from top to bottom, a rubber layer 14b, a cellular layer 16b, a wax layer 18b, cellular layer 16b, rubber layer 14b, etc.

Figure 7:
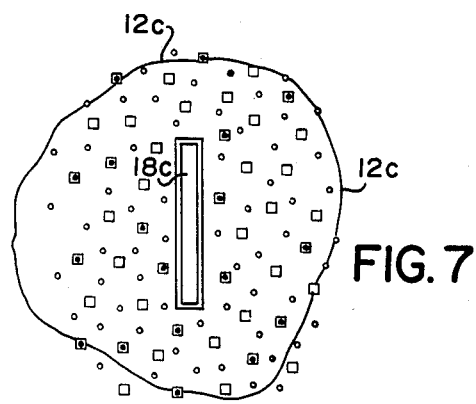
FIG. 7 is an enlarged fragmentary view illustrating the formation of a heating element according to the present invention using particulate material.

In FIG. 7, there is illustrated a form of heating element or cartridge formed of particles of the various elements identified above. For example, particles of rubber in granular form and mixed with a lubricant, and particles of cellular material in granular form can be interspersed about a wax core. Water may likewise form part of this mixture. The entire heating element is enclosed within a paper layer.

In each of the foregoing embodiments, water is interspersed in the cellular material. It will be appreciated that water reaches a boiling point at about 212° F. and that, at such temperature and above, water would expand to steam. This is undesirable and, accordingly, the forms of the present invention illustrated in FIGS. 1 through 7 are preferably not used where temperature requirements exceed the boiling point of water. As will be seen from the ensuing description, the embodiments of the invention illustrated in FIGS. 13 et seq. are not limited with respect to the temperature to which they may be heated. Thus, those embodiments may be used for applications requiring temperatures both below and above the boiling point of water. In certain applications, as indicated below, it may be desirable to substitute petroleum based oil or vegetable oil for the water.

Referring now to FIGS. 8 through 12, which illustrate various applications of the heating element or cartridge of FIGS. 1 through 4, the layered heating element of FIGS. 5 and 6 and the particulate heating element of FIG. 7, it will be appreciated that the cartridges of FIGS. 1 through 4 may be heated by subjecting them to high-frequency microwave radiation. Once heated, they may be inserted into the hollow cylindrical sleeves of conventional hair rollers, for example, those formed of plastic construction illustrated as R in FIG. 8. In this manner, the heating element cartridge radiates heat into the plastic sleeve which, in turn, radiates heat outwardly into the hair rolled thereabout.

Figure 9:
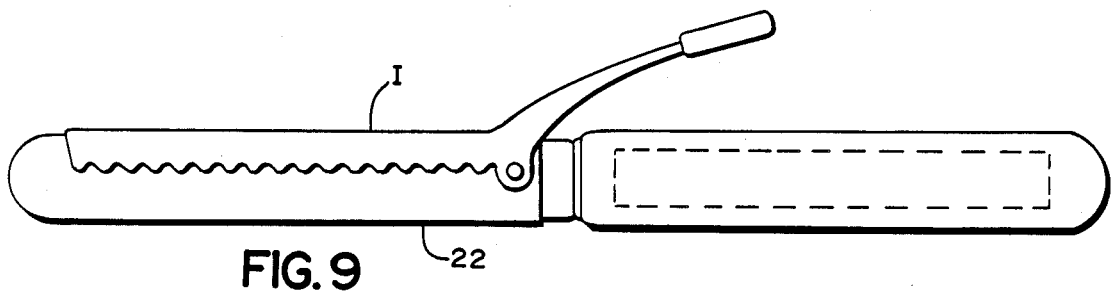

In FIG. 9, there is illustrated a hair curling iron I having a tubular end 22 about which hair is curled. In this form, the tubular end is hollow and adapted to receive a heating element cartridge of the foregoing described type upon its removal from the curling iron handle. In this manner, heat radiates from the cartridge within the tubular end, through the tubular end and into the hair being curled.

Figure 10:
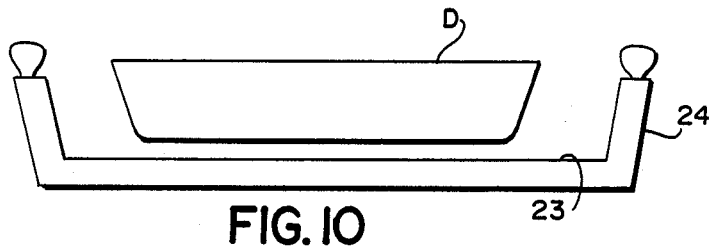

In FIG. 10, there is illustrated a warming dish D formed of layered material, such as described and illustrated FIGS. 5 and 6. In this form, the layered material is formed with a base 23 and an upstanding margin 24. In use, the heating element is disposed in a conventional microwave oven and removed and the dish to be warmed is placed within the element. The heat from the element radiates into the dish, maintaining it in a desired heated condition.

Figure 11:
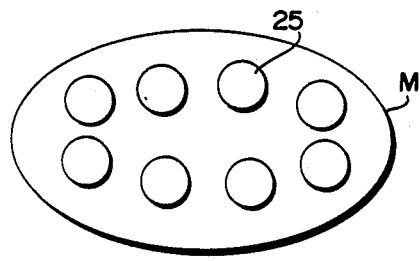

In FIG. 11, there is illustrated a massager M comprised of an outer covering in which particles of material, such as illustrated in FIG. 7, are encapsulated in discrete pockets or pouches 25 and interspersed throughout the massager. Thus, the massager may be disposed in a microwave oven and removed and applied to the individual.

Figure 12:
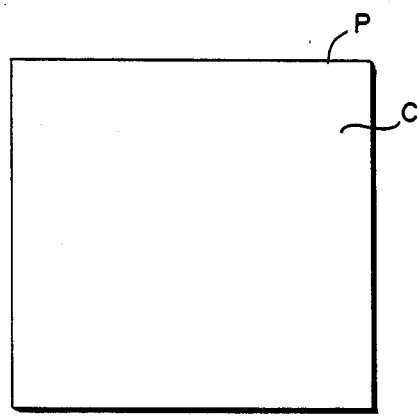

In FIG. 12, there is illustrated a heating pad P comprised of a plurality of the layered materials described and illustrated in FIGS. 5 and 6. The heating pad may be closed with a covering material, for example, terrycloth C. In use, the entire pad may be disposed in a microwave oven to heat the heating element. Upon its removal from the microwave oven, the heating pad may be applied to the individual, with the heat radiating from the heating element to afford therapeutic results.

Referring now to FIG. 13, there is illustrated a cartridge or heating element generally designated 30 disposed within a conventional hair roller 32, for example, a hair roller in the shape of a generally elongated cylindrical sleeve having enlarged ends 34, preferably knurled, and formed of plastic material. The roller has an outer sleeve 33, for example, a silicone sleeve, for purposes of affording good traction with hair. The cartridge 30 is preferably removably receivable within sleeve 32 and suitable releasable retention means, for example, mating parts affording a snap fit, not shown, may be optionally employed.

In this form, the heating element or cartridge 30 is preferably comprised of a central wood dowel 36, which is axially bored to form a central passageway 38, an overlying annular layer of high carbon content rubber material 40, and an outer covering of paper 42, the rubber and paper layers being of like material, as described previously with respect to the embodiments hereof illustrated in FIGS. 1-4. As illustrated, the ends of paper 42 at opposite ends of the cartridge overlap one another and are secured each to the other, for example, by glue, not shown. Also, a high-temperature lubricant 43 is provided between wood dowel 36 and rubber 40 for the purposes stated previously.

In this form, cartridge 30 may be heated by subjecting it to high-frequency microwave radiation, for example, by disposing it in a microwave oven. The central passage 38 through wood dowel 36 and the corresponding opening through the overlapping paper at the ends of the cartridge enable the heat generated in the microwave oven to dissipate, thus avoiding hot spots and the rapid buildup of heat to high undesirable temperatures. Similarly, the paper enclosing the heating element dissipates the heat for like purposes. Upon removal of the cartridge from the microwave oven, the cartridge is inserted into roller sleeve 32. Releasable retention means may be provided as desired, as indicated previously. Roller 32 is then applied to the hair and heat radiating from the cartridge penetrates the roller sleeve material into the hair. As in the previous embodiments, it has been found that the heat retention characteristics of the cartridge illustrated in FIG. 13 and 14 are substantial and far exceed those of present-day conventional plastic rollers heated by conventional electrically-operated heating elements.

Referring now to FIG. 15, there is illustrated a hair roller 32a in which the cartridge 30a is permanently disposed. Cartridge 30a in this form is similar to the cartridge 30 of the previous form. End retention plugs 44, formed, for example, of a suitable high-temperature plastic material or epoxy are used to secure the cartridge 30a within the roller. In this form, the central opening 38a is combined through the end plugs such that the heat from the interior of the cartridge can be dissipated. In use, the roller with integral internal cartridge 30a, is disposed in the microwave oven, heated and applied similarly as in the previous embodiment.

It will be appreciated that the foregoing embodiments of FIGS. 13-15 are adaptations of the heating element hereof to existing hair rollers. The cartridge hereof, however, may itself form a hair roller. Thus, in the form illustrated in FIG. 16, the heating element is similar to the heating element illustrated in FIG. 13 but has the dowel 38b extended to project from its opposite ends, as indicated at 50. Enlarged diameter end retention buttons 51 having central openings close the opposite ends of the cartridge, the central openings in buttons 51 receiving the projecting ends 50 of dowel 38b. In this form, a sleeve 52 is disposed about the exterior paper covering 42b, sleeves 52 preferably comprising a silicone sleeve for providing traction when the roller is applied to the hair. In this form, it will be seen that a central opening is not provided through wood dowel 36b. Heat, however, dissipates through the wood dowel through end surfaces 50 exposed through buttons 51. The end retaining buttons 51 may be formed of wood or other material, such as plastic, as desired.

Another hair care product with which a heating element constructed in accordance with the present invention may be provided is a hair clip, generally designated 60, illustrated in FIG. 17. In FIG. 17, hair clip 60 includes a pair of plastic finger grips 70 hinged one to the other at 72. The clips are spring-loaded, by means not shown, and suitable stops, also not shown, are provided to retain the grips in the position illustrated. The grips have curvilinear or arcuate sections 74, the inside concave and opposing surfaces of which mount a heating element 76 constructed in accordance with the present invention. Heating element 76 comprises an inner layer of high carbon content rubber 78 encapsulated, at least on one side, but preferably on both sides, by a paper material such as fish paper. It has been found that the heat retention capabilities of the high carbon content rubber 78, when activated by high-frequency microwaves, is sufficient to radiate heat when applied about a conventional roller 80 disposed between the jaws of the hair clip.

Referring now to FIG. 18, there is illustrated a hair clip, generally designated 90, for partially encompassing a hair roller 92 about which hair has been rolled. In this form, there is provided a plastic casing in a generally semi-circular form, mounting along its inside surface a heating element similar to the heating element illustrated in the hair clip of FIG. 17.

That is, the heating element comprises an inner core of high carbon content rubber 94, encompassed on at least one side and, preferably on both sides, by paper 96, for example, fish paper. The construction of this clip is such that, after heating the high carbon content rubber 94 in a microwave oven, the clip may be applied directly about the rolled hair on roller 92. The clip has a circumferential extent slightly greater than 180° whereby it can be releasably retained on the roller. As in the previous embodiment, it has been found that the heat retention characteristics of the rubber are sufficient to enable the clip to radiate heat into the hair for an extended period of time.

Referring now to FIG. 19, there is illustrated in more detail the application of a heating element of the present invention to a curling iron. In this form, the elongated barrel B of the curling iron comprises an outer sleeve 100, for example, formed of Teflon ®, surrounding an intermediate annular layer of high carbon content rubber 102 and a central core formed by a wood dowel 104. As illustrated, the end of the wood dowel 104 projects beyond at least one end of the Teflon ® sleeve and is thus exposed to dissipate the heat as in prior embodiments. Lubricant is applied between the wood dowel and the rubber, as in the prior embodiments. Sleeve 100 may be provided with a silicone sleeve to provide traction with the hair. In this form, barrel B is removable from the handle of the curling iron and may be placed in a microwave oven for heating by high-frequency microwave radiation. As in the previous embodiments, the high carbon content rubber is rapidly heated and, upon removal from the microwave oven, the barrel may be placed in the curling iron handle and the curling iron applied to the hair. The heat retained by the high carbon content rubber 102 thus radiates outwardly through sleeve 100 into the hair.

In accordance with another aspect of the present invention, it has been found that another material which has high heat-retention capability is clay. Various clays may be used, for example, montmorillonite, kollinite, nacrite, bentonite, dickite, holloysite, and illite, are suitable. Clay may be advantageously used because it is a low-cost product, may be provided in particulate form, is capable of being mixed with water and other minerals and oils and is flexible and moldable. Clay may be used as a substitute for the cellular material described in connection with the embodiments hereof illustrated in FIGS. 1 through 6 or for the heat retention rubber material, as set forth above in the embodiments hereof illustrated in FIGS. 13 through 19. When used as the heat retention vehicle in the various rollers and clips, particulate dry clay, constituting about 65–75% of the total mixture by L volume and passable through a 30–50 mesh screen, may be mixed with water, preferably distilled water, or, in lieu of water, petroleum or vegetable oil. The water or oil may be in an amount about 15–20% of the total mixture. The mixture may also include about 5–15% rubber particles for enhanced heat retention effects. High-temperature lubricant may also be added to the high carbon content rubber particulate material in the amount of about 5% by volume, the lubricant being mixed with the granular rubber before mixing with the clay. Where lower temperature applications are needed, the particulate high carbon content rubber may be replaced with additional clay in the same amount.

Accordingly, in the embodiments hereof illustrated in FIGS. 1 through 6, this mixture of clay, water, high carbon content rubber and high temperature lubricant may be used in lieu of the cellular material. With respect to FIGS. 13 through 19, this material may be used in lieu of the rubber material, the other materials remaining the same.

With respect to the plastic rollers per se and other plastic materials, for example, used in the hair clips of FIGS. 17 and 18, high temperature resistant plastic is preferred. For example, such plastic material may comprise nylon, polycarbonates, polyolefins, polyesters, polypropylenes, polyethylene and other thermosetting plastics.

In FIG. 21, there is provided a heating element 120, constructed in accordance with the present invention, as part of a buffing pad. Here, clay is encapsulated between a pair of plastic sheets 122 wherein the sides of the sheets are open. Alternatively, the plastic layers may be perforated. The clay material may be mixed with aromatics or therapeutic minerals. The outer cover may be treated with an astringent whereby the skin may be cleansed by application of the buffing pad with the astringent and minerals.

Another application of the heating element hereof may be provided in the form of a mud pack. In this form, not shown, granular clay having certain minerals interspersed within it may be disposed in a container or covering. For example, clay can be mixed with other compositions to provide a pleasing odor, for example, perfume, or it may be mixed with medicinal and therapeutic preparations for application to the individual's skin. Thus, the mud pack containing the clay mixture may be disposed in the microwave oven and heated. Once heated, the covering may be removed from the clay and the clay applied directly to the individual's skin in conforming relation thereto. The heat from the clay radiates outwardly and is applied to the individual's skin.

A still further application of the heating element of the present invention is a hair straightener. Here, clay is disposed in a thin flat plastic bag 130. Upon heating the clay in the microwave oven, the clay and bag may be folded about a centerline 132, with the hair to be straightened disposed between the leaves of the folded bag illustrated in FIG. 22b. In this manner, the hair disposed between such leaves can be straightened by the application of heat radiating from the clay through the covering.

Where clay is used in its layered form, it is preferably to employ about 60–65% dry air-floated 200 mesh or better clay material, with an addition of about 15–20% of water, preferably distilled water. The remaining constituents may be about 5–15% high content carbon rubber, where added or heat retention is required, and about 5% lubricant, i.e., a natural oil. In those embodiments where the enclosure for the clay is removed, i.e., the mud pack, or where the clay is disposed in a perforated container and constituents of the clay are disposed in contact with the skin, the clay composition may be the same as described above, with the exception that (1) instead of water, aloe vera oil, glycol, glycerin or other non-allergenic material compatible with the skin may be used and (2) the 5–15% high carbon content rubber may be removed with an equal amount of clay substituted therefor. With respect to the lubricant, a natural oil base may be substituted for the petroleum base oil. When the clay is used in the skin care field, 5–10% of its constituents may comprise minerals, oils, herbs, analgesics, purifiers and the like.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A multi-layer microwave heatable element for use in hair care comprising:

a first layer formed of a material having heat dissipative properties;
a second layer overlying said first layer and formed of a material reactive to high frequency microwave radiation to rapidly elevate its temperature;
an outer layer of material overlying said second layer for maintaining said first and second layers substantially air tight and through which heat may be dissipated; and
an annular sleeve forming a hair roller, said first layer constituting a core, and said second and third layers constituting annular layers surrounding said core whereby said layers form a generally cylindrical cartridge receivable within said sleeve for heating said sleeve.

2. An element according to claim 1 wherein said outer layer of material extends to overlie the ends of said cartridge.

3. An element according to claim 1 wherein said cartridge has an axial extending passage therethrough from one end to the opposite end providing a passage for dissipating heat when said cartridge is subjected to microwave radiation.

4. An element according to claim 3 including means for permanently sealing the ends of said sleeve with said cartridge contained therein and with said axial extending passage opening through said sealed ends, thereof.

5. An element according to claim 1 wherein said core is formed of wood.

6. An element according to claim 1 wherein said second annular layer is formed of rubber.

7. An element according to claim 1 wherein said third layer is formed of paper.

8. An element according to claim 1 wherein said first, second and third layers are formed of wood, rubber and paper, respectively.

9. An element according to claim 1 including a lubricant disposed between said first and second layers.

10. A multi-layer microwave heatable element for use in hair care comprising:
a first layer formed on a material having heat dissipative properties;
a second layer overlying said first layer and formed of a material reactive to high frequency microwave radiation to rapidly elevate its temperature; and
an outer layer of material overlying said second layer for maintaining said first and second layers substantially air tight and through which heat may be dissipated, said second layer being formed principally of a clay material.

11. An element according to Claim 10 wherein said second layer comprises clay in percent by volume about 65-75% clay, about 15-20% water, about 5-15% high carbon content rubber and about 5% high temperature lubricants.

12. An element according to claim 10 wherein said second layer comprises in percent by volume about 65-75% clay, about 15-20% petroleum or vegetable oil, about 5-15% high carbon content rubber and about 5% high temperature lubricant.

13. A microwave-activated heating element comprising:
a core formed of wood;
an annular layer formed of rubber and overlying said core; and
an annular layer of paper overlying said annular rubber layer, said wood core, at least in part, being exposed to ambient conditions.

14. A heating element according to claim 13 wherein said wood core is exposed to ambient conditions through at least one end thereof.

15. A heating element according to claim 14 wherein said wood core has a projection at one end thereof for projecting beyond the ends of said annular layers, and a sleeve formed of plastic material and receiving said core.

16. A multi-layer microwave heatable element for use in hair care comprising:
a first layer formed of a wax material;
a second layer overlying said first layer and formed of a rubber material reactive to high-frequency microwave radiation to rapidly elevate its temperature;
a third layer of cellular material overlying said first layer of rubber material; and
an outer layer of material overlying said first second and third layers for maintaining said element substantially airtight and through which heat may be dissipated.

17. An element according to claim 16 including an annular sleeve forming a hair roller, said first layer constituting a core, and said second, third and fourth layers constituting annular layers surrounding said core whereby said layers form a generally cylindrical cartridge receivable within said sleeve for heating said sleeve.

18. An element according to claim 16 wherein said outer layer of material extends to overlie the ends of said cartridge.

19. A hair clip for use in a hair roller comprising:
a pair of finger grips;
means for securing said grips one to the other for pivotal movement about an axis;
a pair of arcuate microwave heatable sections secured to said pair of grips, respectively, said sections having their concave portions in opposition one to the other whereby, upon pivotal movement of said finger grips, said sections are movable toward and away from one another for releasably clamping about a hair roller;
said sections being formed of an arcuate core material reactive to high-frequency microwave radiation to rapidly elevate its temperature; and
paper overlying at least one of the arcuate section surfaces of each of said core material.

20. A hair clip according to claim 19 wherein said core comprises a high carbon content rubber.

21. A hair clip according to claim 19 wherein said grips carry arcuate extensions thereof in generally conformal relation to the convex surfaces of said sections, affording a cover for each of the convex surfaces thereof.

22. A hair clip according to claim 19 wherein said core is formed principally of a claim material.

23. A hair clip for use in a hair roller comprising:
a generally semi-cylindrical elongated housing;
a generally semi-cylindrical microwave heatable section secured to the concave surface of said housing;
semi-cylindrical core material reactive to high-frequency microwave radiation to rapidly elevate its temperature; and
paper disposed overlying at least one of the semi-cylindrical surfaces of said core material.

24. A hair clip according to claim 23 wherein said core comprises a high carbon content rubber.

25. A hair clip according to claim 23 wherein said core is formed principally of a clay material.

26. A microwave heatable element comprising:
a layer of clay material reactive to high-frequency microwave radiation for heating the clay material layer; and
means for encapsulating said layer of clay material to preclude egress of clay material from the element and through which heat may radiate from the heated clay.

27. A heating element according to claim 26 including a covering for said encapsulated clay material whereby said element may constitute a heating pad.

28. A heating element according to claim 26 wherein said encapsulating means is perforated, said clay being mixed with a material having one of odoriferous, therapeutic or medicinal characteristics, and a cover for said encapsulating means whereby said one material may be effective through said covering.

29. A heating element according to claim 28 wherein said layer of material comprises in percent by volume about 60-65% clay, about 15-20% water, a petroleum base oil or vegetable oil, about 5-15% high carbon content rubber and about 5% high temperature lubricant.

* * * * *